United States Patent
Mace et al.

(10) Patent No.: US 9,480,670 B2
(45) Date of Patent: Nov. 1, 2016

(54) REDUCTION OF RISK OF OBESITY

(75) Inventors: Catherine Mace, Lausanne (CH); Olivier Aprikian, Dublin, OH (US)

(73) Assignee: Nestec S.A., Vevey (CH)

( * ) Notice: Subject to any disclaimer, the term of this patent is extended or adjusted under 35 U.S.C. 154(b) by 182 days.

(21) Appl. No.: 13/260,842

(22) PCT Filed: Mar. 26, 2010

(86) PCT No.: PCT/EP2010/054025
§ 371 (c)(1),
(2), (4) Date: Sep. 28, 2011

(87) PCT Pub. No.: WO2010/112429
PCT Pub. Date: Oct. 7, 2010

(65) Prior Publication Data
US 2012/0029080 A1 Feb. 2, 2012

(30) Foreign Application Priority Data
Apr. 1, 2009 (EP) ..................................... 09157086

(51) Int. Cl.
*A61K 31/202* (2006.01)
*A23L 1/29* (2006.01)
*A23L 1/30* (2006.01)

(52) U.S. Cl.
CPC .............. *A61K 31/202* (2013.01); *A23L 1/296* (2013.01); *A23L 1/3008* (2013.01); *A23V 2002/00* (2013.01)

(58) Field of Classification Search
None
See application file for complete search history.

(56) References Cited

U.S. PATENT DOCUMENTS

| 6,326,355 | B1 * | 12/2001 | Abbruzzese et al. ........... 514/23 |
| 6,753,350 | B1 * | 6/2004 | Hansen et al. ................ 514/560 |
| 6,787,158 | B1 | 9/2004 | Erdmann et al. |
| 2004/0265462 | A1 * | 12/2004 | Carlson .................... A23L 1/296 426/580 |
| 2005/0054724 | A1 * | 3/2005 | Mustad et al. ................ 514/547 |
| 2007/0104856 | A1 * | 5/2007 | Standal ..................... A23D 9/00 426/643 |
| 2007/0203237 | A1 | 8/2007 | Brenna et al. |
| 2007/0203238 | A1 | 8/2007 | Jouni et al. |
| 2008/0269117 | A1 | 10/2008 | Hageman |

FOREIGN PATENT DOCUMENTS

| EP | 2008054192 | 5/2008 |
| WO | 2007100561 | 9/2007 |
| WO | EP 2008071667 | 6/2008 |

OTHER PUBLICATIONS

Ailhaud et al., "Temporal changes in dietary fats: Role of n-6 polyunsaturated fatty acids in excessive adipose tissue development and relationship to obesity," Progress in Lipid Research, Pergamon Press, Paris, FR, vol. 45, No. 3, May 1, 2006, pp. 203-236, XP025038617.
Das et al., "Is metabolic syndrome X a disorder of the brain with the initiation of low-grade systemic inflammatory events during the perinatal period?", Journal of Nutritional Biochemistry, vol. 18, No. 11, Oct. 24, 2007, pp. 701-713, XP022313149.
Search Report for International Application No. PCT/EP2010/054025 mailed Jun. 8, 2010.
WebMD Article Entitled "How Triglycerides Affect Your Risk of Diabetes", printed Nov. 5, 2014 from http://www.webmd.com/cholesterol-management/diabetes, 3 pages.
ScienceDaily Article Entitled "New Link Found Between Obesity and Insulin Resistance", printed Nov. 5, 2014 from http://www.sciencedaily.com/releases/2011/08/110802125551.htm, 3 pages.

\* cited by examiner

*Primary Examiner* — James D Anderson
*Assistant Examiner* — Meghan Finn
(74) *Attorney, Agent, or Firm* — K&L Gates LLP

(57) ABSTRACT

A nutritional composition comprising a significant amount of arachidonic acid (ARA) is described. Such nutritional composition is particularly suitable for infants below the age of 3 years, preferably between birth and 12 months of life. The composition can be used to reduce the risk of developing overweight/obesity and/or insulin resistance later in life.

3 Claims, 5 Drawing Sheets

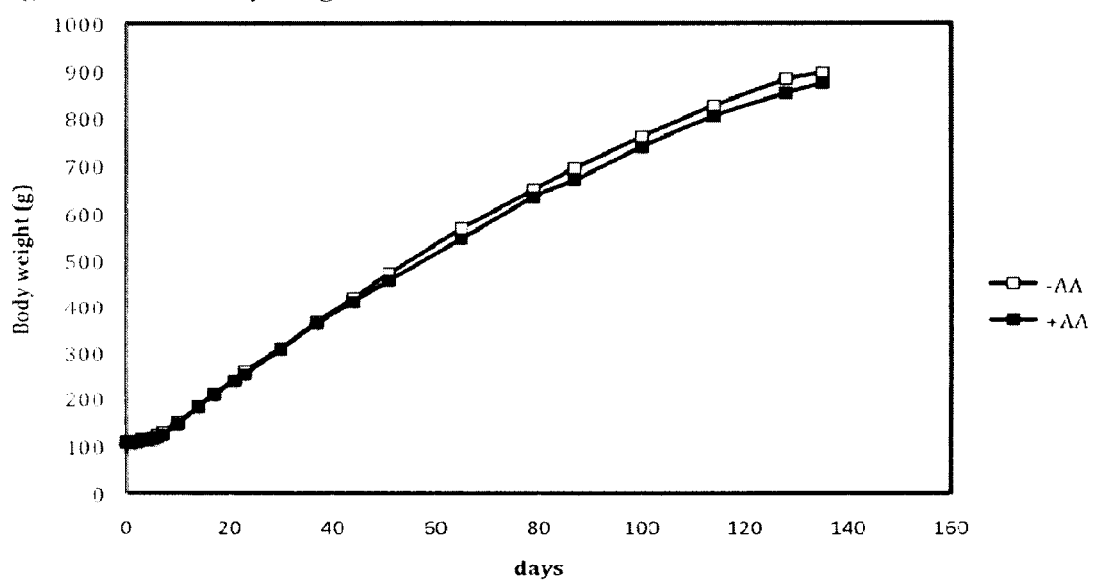
Figure 1: Mean body weight

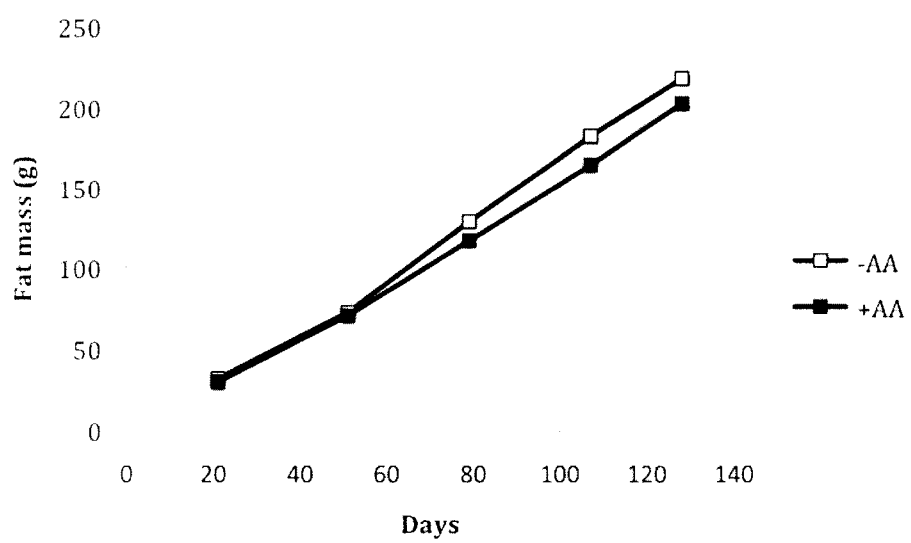
*Figure 2: Fat mass (g) evolution from d21 to 128*

Figure 3: Fat mass (%) at d79, d107 and d128, Mean
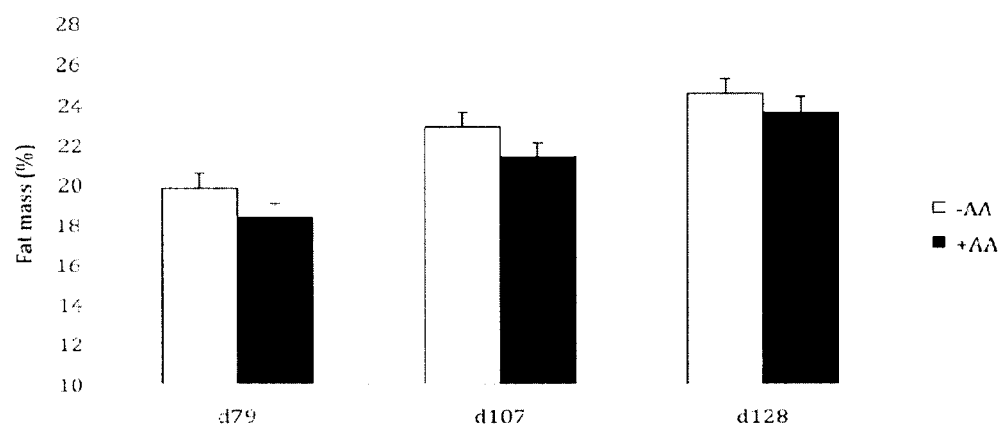

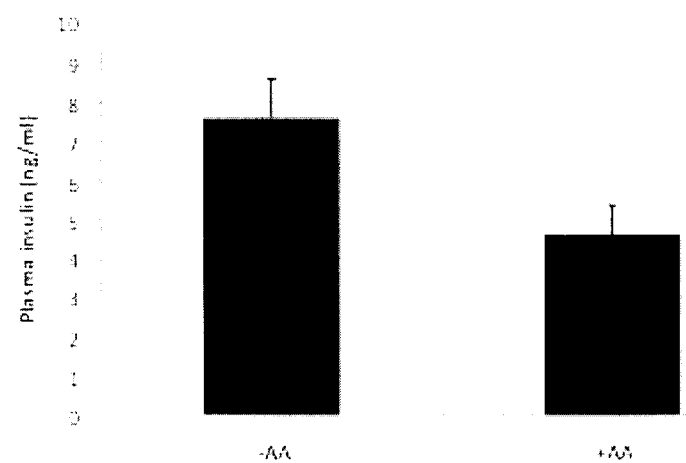
Figure 4: Plasma insulin levels at d136

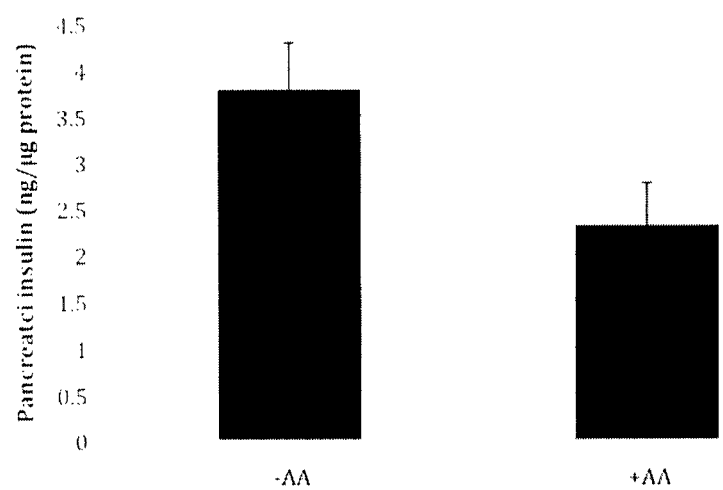
Figure 5: Pancreatic insulin content at d136

REDUCTION OF RISK OF OBESITY

CROSS REFERENCE TO RELATED APPLICATIONS

The present application is a National Stage of International Application No. PCT/EP2010/054025, filed on Mar. 26, 2010, which claims priority to European Patent Application No. 09157086.1, filed on Apr. 1, 2009, the entire contents of which are being incorporated herein by reference.

This invention relates to the use of a nutritional composition such as an infant formula or a baby food, comprising an n-6 long chain polyunsaturated fatty acid to reduce the risk of the infant developing obesity and insulin resistance later in life.

Mother's milk is recommended for all infants. However, in some cases breast feeding is inadequate or unsuccessful or inadvisable for medical reasons or the mother chooses not to breast feed either at all or for a period of more than a few weeks. Infant formulas have been developed for these situations. Similarly, the infant's nutritional needs remain specific until early childhood. There are situations where the nutritional needs cannot be adequately covered by family foods. Therefore, nutritionally-balanced baby foods designed according to the baby's particular needs are the most appropriate complementary source of nutrition during infancy and early childhood.

The prevalence of obesity and overweight in adults, children and adolescents has increased rapidly over the past 30 years in the United States and globally and continues to rise. Childhood overweight and obesity currently affects 18 million children under age 5 worldwide. Almost 30% of US children and adolescents and between 10 and 30% of European children are overweight or obese.

Increasingly it is believed that the first 6 months of life represent one of the most important postnatal periods for human fat mass development and consequently may be a critical window for programming excess of adiposity later in life. Moreover, human epidemiological data and animal studies evidence that elevated body weight at birth or during infancy are associated with a risk for development of diseases such as insulin resistance syndrome (also called metabolic syndrome), Type 2 diabetes and cardiovascular problems later in life.

Massiera et al. investigated the influence of the long chain, polyunsaturated fatty acid arachidonic acid C20:4, n-6 (ARA) on the differentiation of clonal preadipocytes. They found that, compared to a combination of specific agonists to both peroxisome proliferator-activated receptors $\delta$ and $\gamma$ or to saturated, mono-unsaturated and n-3 polyunsaturated fatty acids, ARA substantially promoted the differentiation of clonal preadipocytes. They further discovered that this effect was blocked by cyclooxygenase inhibitors and mimicked by carbacyclin suggesting a role for the prostacyclin receptor and activation of the cyclic AMP-dependent pathways that regulate the expression of CCAAT enhancer binding proteins $\beta$ and $\delta$ implicated in adipogenesis. In a study in which different groups of lactating mice were fed either a diet rich in linoleic acid (a precursor of ARA) or an isocaloric diet containing a mixture of linoleic acid and $\alpha$-linolenic acid, they found that body weight from weaning onwards, fat mass, epididymal fat pad weight and adipocyte size at 8 weeks of age were higher with the linoleic acid-enriched diet. When the same experiment was carried out using prostacyclin receptor-deficient mice, no difference was observed between the groups indicating that the prostacyclin signaling contributes to adipose tissue development. The authors comment that these results may be significant in view of the relatively high content of linoleic acid of infant formula, linoleic acid being a precursor of ARA.

In WO2008/054192, it is claimed that the whole adipose tissue mass of infants is not a good predictor to determine the risks of diseases later in life and that it is rather the accumulation of visceral fat mass in early infancy should be considered. It has been demonstrated that visceral adipocyte count is primarily determined during infancy and it follows that it would be useful to be able to control adipogenesis during this period. Among the possible solutions proposed in WO2008/054192, it is suggested that administration of the n-3 long chain polyunsaturated fatty acids docosahexaenoic acid, stearidonic acid, docosapentaenoic acid and/or eicosapentaenoic acid may reduce accumulation of visceral fat mass whilst maintaining normal growth and development. It is, however, recommended not to include ARA on the basis that ARA counteracts the effect of the n-3 long chain polyunsaturated fatty acids.

SUMMARY OF THE INVENTION

Surprisingly, the present inventors have discovered that a moderate intake of arachidonic acid during the early stages of life reduces accumulation of total fat mass and improve insulin sensitivity later in life.

Accordingly, the present invention provides the use of arachidonic acid in the manufacture of a nutritional composition for administration to an infant in the first 6 months, first year or first 3 years of life of the infant so as to reduce the risk of development of obesity and insulin resistance later in life. The invention is particularly targeted at, but not limited to, infants having a predisposition to obesity and insulin resistance syndrome.

The invention further extends to a method of reducing the risk that an infant will develop obesity and insulin resistance later in life comprising feeding to the infant in the year of its life a nutritional composition comprising arachidonic acid.

Preferably the nutritional composition includes arachidonic acid in an amount sufficient to provide a daily dose of between 5 and 100 mg per kg per day. In terms of a nutritional composition providing complete nutrition such as an infant formula, this can correspond to an arachidonic acid content of between 0.6% (w/w) and 1.2% (w/w) expressed as a percentage of total fatty acid content of the composition

BRIEF DESCRIPTION OF THE DRAWINGS

FIG. 1 shows the evolution of body weight of two groups of guinea pig pups fed different diets over the first 136 days of life.

FIG. 2 shows the evolution of fat mass in the two groups expressed in grams from day 21 to day 128.

FIG. 3 shows the evolution of fat mass in the two groups expressed as a percentage of total body weight at day 79, day 107 and day 128.

FIG. 4 shows the mean plasma insulin levels of the two groups at day 136.

FIG. 5 shows the pancreatic insulin contents of the two groups at day 136.

DETAILED DESCRIPTION OF THE INVENTION

In this specification, the following expressions have the meanings assigned to them below:—

"ARA" or "AA" means arachidonic acid (C20:4n-6);
"DHA" means docosahexaenoic acid (C22:6n-3)
"infant" means a child under the age of 12 months and "infancy" shall be construed accordingly;

"later in life" means, in the context of an infant, any point in life after completion of infancy. One example of such a point would be at the age of the adiposity rebound which, in human infants, typically occurs between the ages of five and six years.

"predisposition to obesity" includes all factors in the infants or foetus having an influence on the development of an overweight or obese status later in life. Such factors may include genetic factors, inherited factors, acquired factors, environmental factors, metabolic factors, geographical, social and/or economic factors that have been shown to predispose the infants or foetus to the development of overweight or obesity. The definition of obesity or overweight is based on the admitted international standards (taking into account the body-mass index).

"insulin resistance" is the inability of cells from the body to respond to insulin. Over time, this results in hyperinsulinemia (excess of insulin in the blood). Insulin resistance is associated with abdominal obesity, high blood pressure, high triglycerides, low HDL cholesterol. These conditions are part of a constellation of disorders called "insulin resistance syndrome" or "metabolic syndrome". As for the predisposition to obesity, the predisposition to insulin resistance take into account all factors impacting the risk of developing insulin resistance.

All percentages and ratios are by weight unless otherwise specified.

A nutritional composition for use according to the present invention may be any product which is suitable for consumption by an infant in the first year of life. Examples of such products include infant formula, follow-on formula, growing up milks, infant cereals, fruit and vegetable purées and baby meals such as those mixtures of meat or fish with vegetables commonly sold in single ready to serve portions.

Preferably, a nutritional composition for use according to the present invention is a complete nutritional composition i.e. a composition which supplies all the nutritional requirements of the infant such as an infant formula or a follow-on formula. Such a composition will comprise at least 50 mg of ARA in the daily quantity of nutritional composition, preferably at least 340 mg and most preferably between 500 and 850 mg of ARA in the daily quantity of nutritional composition.

In one embodiment of the invention, the nutritional composition in the invention comprises more arachidonic acid in a quantity such as to provide more arachidonic acid than the average arachidonic quantity provided by the standard or the average diet for the age group of the mammal. Such enhanced delivery of arachidonic acid to the mammal by the nutritional composition of the invention is believed to induce the described effect. Such standard diet consider herewith delivers between 0 and less than less than 34 mg of ARA per day per kg of mammal. In some instance the standard diet delivers between 5 and less than 20 mg of ARA per day per kg of mammal. In such embodiments, the composition of the invention may contain more ARA than the quantity able to deliver such above ranges when the composition is consumed in the recommended daily dose (pending on age, nature of the composition, etc, . . . ). Hence, in one embodiment, the composition of the invention delivers more than what is provided by the standard diet.

In the theoretical example of a baby food for a baby of 10 kg: The daily ARA intake of the baby in the regular diet may be 50 mg/day. The target daily intake of ARA for this baby, according to the invention, may be at or at least at 500 mg/day (=50 mg/day/kg of the baby). Hence 450 mg, or at least 450 mg of ARA, need to be provided daily by the composition of the invention. The composition of the invention may be recommended to be consumed at a dose of 450 g/day. Hence the concentration of ARA in the composition of the invention may be at least 1 mg ARA/g of composition. In other embodiments of the invention, the composition comprises between 0.5 mg ARA/g of composition and 3 mg ARA/g of composition, preferably between 1.5 and 2 mg ARA/g of composition. The optimal ranges are specific to the type of nutritional composition and daily recommended quantity consumed. For other compositions of the invention intended for different target babies, the composition comprises between 0.1 mg ARA/g of composition and 1.5 mg ARA/g of composition. Very concentrated compostions of the invention may be considered for further targets at between 5 mg ARA/g of composition and 10 mg ARA/g of composition, preferably between 6 and 8 mg ARA/g of composition.

In one embodiment of the invention the quantity of ARA comprised in the nutritional composition is between 0.30 mg and 0.85 mg of ARA per kcal of nutritional composition, preferably between 0.3 mg and 0.7 mg. Such ranges are believed to represent an appropriate balance between beneficial effect, taste and cost while not impacting significantly the total caloric content.

In one embodiment of the invention, the ARA content in the composition is in the range from 0.1% to 2% of ARA expressed as a percentage of total fatty acids content of the composition, more preferably between 0.6% to 1.2%. Such ranges are believed to represent an appropriate balance between beneficial effect, taste and cost.

The source of ARA in the nutritional composition of the invention may originate from the ingredients of the composition and/or can be added as an independent isolated nutrient. Preferably the composition comprises ARA from the ingredients and is supplemented with isolated ARA to achieve the target level of ARA to be delivered to the infant or to achieve the target content of ARA in the composition.

ARA is typically derived from fungal biomass, for example by cultivation of species of *Mortierella alpina* as is well known and described in the art. ARA may be included in nutritional compositions for use according to the invention by addition of small amounts of concentrated ARA oil such as the ARA oil sold under the trade mark ARASCO® by Martek Biosciences Inc. Alternatively, the ARA may be recovered from the biomass using a transfer oil and incorporated in the nutritional composition along with the transfer oil as described in EP 1239022 the contents of which are incorporated herein by reference.

In one embodiment of the invention the composition comprised a source of protein, a source of lipids and a source of carbohydrate. The lipid source comprises arachidonic acid in an amount such as to provide between 5 mg and 100 mg of arachidonic acid per kg per day to the mammal, preferably between 35 and 85 mg/kg/day, most preferably between 50 and 60 mg/kg/day. The content of ARA in the composition can be adjusted to take into account the daily diet of the target mammal and its age and weight.

In one embodiment of the invention the content of ARA in the composition is adjusted to take into account the ARA in the daily diet coming from sources other than the composition itself, and optionally further adjusted for age and weight. This can insure that the total ARA daily intake stays within the admitted limits for each age/weight group in order to not induce adverse effects.

In a preferred embodiment of the invention, the ARA is incorporated as an isolated compound (supplementation) in a composition, preferably a solid food, that already comprises a significant amount of fatty acids (i.e. more than 20% of the total energy comes from fatty acids).

The mammal considered by the present invention is preferably a young mammal, most preferably a human infant between birth and the age of 3 years. Infancy up to that age is indeed regarded as the age group where the impact of specific food for the prevention of obesity and/or insulin resistance is the most effective.

The present invention also relates to the use of the composition in the manufacture of a composition for administration to an infant in the first months years of life, preferably in the first 12 months of life, most preferably the first 6 months, so as to reduce the risk of development of obesity and/or insulin resistance, later in life. In one embodiment the composition of the invention is most suitable for babies up to and including the weaning period. In one embodiment the composition of the infant is an infant formula, infant supplement, infant cereals, infant growing up milk (GUM) or a baby food (GUM encompass milk based compositions for children after 18 months, after 24 months, after 3 years or after 5 years of age). In one embodiment the composition may be administered up to the age of 3 years, up to the age of 5 years in a continuous or discontinuous manner. For example the composition may be administered as an infant formula in younger age (0 to 6, 12 or 18 months) and then between 3 and 5 years at a different regimen. In one embodiment the composition is administered solely after 3 years of age.

Within being bound by the theory, the inventors believe that the effects illustrated in the below described experiments can apply to human infant, especially small infants or toddlers. The risk of developing obesity later in life or of developing overweight can thus be reduced by the administration of the claimed composition. The ARA content values in the composition have been calculated from the experimental data and extrapolated to human infants. The sources of ARA coming from regular food has been taken into account as well as the generally observed maximum amount of ARA in the diet that does not induce adverse effects (estimated at about 100 mg ARA/kg/day).

Preferably the composition of the invention comprises ARA in an amount that is able to deliver more ARA than the ARA usually delivered by regular diet. As such the content of ARA is most preferably adjusted to deliver between 35 and 85 mg ARA/kg/day or between 50 and 60 mg ARA/kg/day. Such amount are believed to represent an appropriate balance between a relatively high amount of ARA (delivering significant beneficial effect) while keeping the amount sufficiently low to not induce adverse effects, especially in infants.

In one embodiment of the invention the composition delivers slightly more ARA than what is usually provided by a standard diet while staying in a range well below what has been show to induce adverse effect. In such embodiment, the composition is able to deliver between 35 and 55 mg ARA/kg/day or between 40 and 50 mg ARA/kg/day.

Particularly, the effect evidenced by the inventors applies to infants having a predisposition to develop obesity later in life or to become overweight.

The risk of developing obesity or overweight can be measured by measuring the occurrence of obesity or overweight in the target population (in comparison to a similar population having not received the composition of the invention).

Preferably, an infant formula or follow-on formula for use in the present invention has a protein content of less than 1.85 g/100 kcal. The detailed make-up of the protein source is not believed to be critical to the present invention provided that the minimum requirements for essential amino acid content are met and satisfactory growth is ensured. Thus, protein sources based on cows' milk proteins such as whey, casein and mixtures thereof may be used as well as protein sources based on soy. However, mixtures of whey and casein proteins are preferred. The casein:whey ratio may lie in the range from 70:30 to 30:70 but is preferably 30:70.

The protein(s) in the protein source may be intact or partially hydrolysed or a mixture of intact and hydrolysed proteins may be used. The protein source may additionally be supplemented with free amino acids if this is necessary to meet the minimum requirements for essential amino acid content. These requirements are published for example in EC Directive 2006/141/EC.

As noted above, the preferred protein source is a mixture of casein and whey proteins. The whey protein may be a whey protein isolate, acid whey, sweet whey or sweet whey from which the caseino-glycomacropeptide has been removed (modified sweet whey). Preferably, however, the whey protein is modified sweet whey. Sweet whey is a readily available by-product of cheese making and is frequently used in the manufacture of nutritional compositions based on cows' milk. However, sweet whey includes a component which is undesirably rich in threonine and poor in tryptophan called caseino-glycomacropeptide (CGMP). Removal of the CGMP from sweet whey results in a protein with a threonine content closer to that of human milk. A process for removing CGMP from sweet whey is described in EP 880902.

If modified sweet whey is used as the whey protein in a mixture of 70% whey and 30% casein, the protein source may be supplemented by free histidine in an amount between 0.2 and 0.5% of total protein content.

A complete nutritional composition for use according to the present invention contains a source of carbohydrates. The preferred source of carbohydrates is lactose although other carbohydrates such as saccharose, maltodextrin, and starch may also be added. Preferably, the carbohydrate content of the nutritional composition is between 9 and 14 g/100 kcal.

A complete nutritional composition for use according to the present invention contains a source of lipids. In addition to ARA, the lipid source may include any lipid or fat which is suitable for use in nutritional compositions to be fed to infants. Preferred fat sources include coconut oil, low erucic rapeseed oil (canola oil), soy lecithin, palm olein, and sunflower oil. The essential polyunsaturated fatty acids linoleic acid (C18:2n-6) and α-linolenic acid (C18:3n-3) will also be included. Preferably, the ratio of linoleic acid: α-linolenic acid in the lipid source is less than 7:1. Small amounts of preformed docosahexaenoic acid (C22:6n-3; DHA) may also be added. Fish oils and single cell microbial oils are suitable sources of docosahexaenoic acid (DHA). If docosahexaenoic acid is present, the ratio of arachidonic acid:docosahexaenoic acid in the lipid source is preferably between 2:1 and 1:1. In total, the lipid content of the nutritional composition may be between 4.4 and 6 g/100 kcal.

A complete nutritional composition will also contain all vitamins and minerals understood to be essential in the daily diet in nutritionally significant amounts. Minimum requirements have been established for certain vitamins and minerals. Examples of minerals, vitamins and other nutrients optionally present in the nutritional composition include vitamin A, vitamin $B_1$, vitamin $B_2$, vitamin $B_6$, vitamin $B_{12}$, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form.

If necessary, the nutritional composition may contain emulsifiers and stabilisers such as soy lecithin, citric acid esters of mono- and di-glycerides, and the like. This is especially the case if the composition is provided in liquid form.

The nutritional composition may optionally contain other substances which may have a beneficial effect such as probiotic bacteria, fibres, lactoferrin, nucleotides, nucleosides, and the like in the amounts customarily found in nutritional compositions to be fed to infants.

Such a nutritional composition may be prepared in any suitable manner. For example, a nutritional composition may be prepared by blending together the protein source, the carbohydrate source, and the lipid source in appropriate proportions. If used, emulsifiers may be included in the blend at this stage. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

The liquid mixture may then be cooled to about 60° C. to about 85° C.; for example by flash cooling. The liquid mixture may then be homogenised; for example in two stages at about 7 MPa to about 40 MPa in the first stage and about 2 MPa to about 14 MPa in the second stage. The homogenised mixture may then be further cooled and any heat sensitive components; such as vitamins and minerals may be added. The pH and solids content of the homogenised mixture is conveniently standardised at this point.

If it is desired to produce a powdered composition, the homogenised mixture is transferred to a suitable drying apparatus such as a spray drier or freeze drier and converted to powder. The powder should have a moisture content of less than about 5% by weight.

If it is desired to produce a liquid composition, the homogenized mixture is filled into suitable containers; preferably aseptically. However, the liquid composition may also be retorted in the container. Suitable apparatus for carrying out filling of this nature is commercially available. The liquid composition may be in the form of a ready to feed composition having a solids content of about 10 to about 14% by weight or may be in the form of a concentrate; usually of solids content of about 20 to about 26% by weight.

Alternatively for older infants such as infants between six and twelve months of age, the desired daily dose of ARA may be achieved by incorporating suitable amounts of ARA in the various foods consumed by the infant during the course of the day such as infant cereals, follow-on formulas and baby meals for example.

The invention will now be further illustrated by reference to the following examples.

Example 1a

An example of the composition of a complete nutritional composition for use according to the invention is given below: (table "Complete nutritional composition")

TABLE

"Complete nutritional composition".

| Nutrient | per 100 kcal | per litre |
|---|---|---|
| Energy (kcal) | 100 | 630 |
| Protein (g) | 1.5 | 9.45 |
| (skimmed milk powder, modified sweet whey) | | |
| free histidine (mg) | 2.5 | 15.8 |
| casein:whey ratio | 40:60 | 40:60 |
| Fat (g) | 5.3 | 33.4 |
| Linoleic acid (g) | 0.7 | 4.4 |
| α-Linolenic acid (mg) | 106 | 668 |
| DHA (mg) | 79 | 500 |
| ARA (mg) | 79 | 500 |
| Linoleic acid: α-Linolenic acid | 6.5 | 6.5 |
| Lactose (g) | 11.6 | 73.1 |
| Minerals and Electrolytes | | |
| Na (mg) | 25 | 158 |
| K (mg) | 89 | 561 |
| Cl (mg) | 64 | 403 |
| Ca (mg) | 64 | 403 |
| P (mg) | 32 | 202 |
| Ca/P | 2.0 | 2.0 |
| Mg (mg) | 6.9 | 43.5 |
| Mn (µg) | 8.0 | 50.4 |
| Vitamins and Trace Elements | | |
| Vitamin A (IU) | 350 | 2205 |
| Vitamin D (IU) | 60 | 378 |
| Vitamin E (IU) | 1.2 | 7.6 |
| Vitamin K1 (µg) | 8.0 | 50.4 |
| Vitamin C (mg) | 10 | 63 |
| Vitamin B1 (mg) | 0.07 | 0.44 |
| Vitamin B2 (mg) | 0.15 | 0.95 |
| Niacin (mg) | 1.0 | 6.3 |
| Vitamin B6 (mg) | 0.075 | 0.47 |
| Folic acid (µg) | 12 | 75.6 |
| Pantothenic acid (mg) | 0.45 | 2.83 |
| Vitamin B12 (µg) | 0.3 | 1.89 |
| Biotin (µg) | 2.2 | 13.9 |
| Choline (mg) | 10 | 63 |
| Inositol (mg) | 5.0 | 31.5 |
| Taurine (mg) | 7.0 | 44.1 |
| Carnitine (mg) | 1.6 | 10.1 |
| Fe (mg) | 1.2 | 7.56 |
| I (µg) | 15 | 94.5 |
| Cu (mg) | 0.07 | 0.44 |
| Se (µg) | 2.0 | 12.6 |
| Zn (mg) | 0.75 | 4.72 |
| Nucleotides | | |
| CMP (mg) | 2.3 | 14.5 |
| UMP (mg) | 1.5 | 9.5 |
| AMP (mg) | 0.7 | 4.4 |
| GMP (mg) | 0.3 | 1.9 |

This nutritional composition may be fed to an infant as the sole source of nutrition from birth to the age of four to six months and subsequently as part of a mixed diet during the introduction of solid foods until weaning is complete at about the age of 12 months.

Example 1b

Another example of the composition of the invention is a solid baby food. The food is presented in glass jars and its basic variant (without supplementation of ARA, hence outside the present invention) is commercialized under the name "3rd FOODS Dinners Chicken Noodle" in the USA. The table below indicates the composition or the baby food. The below described babyfood also comprises 60 mg ARA per container (=per serving). This corresponds to 0.5 mg ARA per kCal of the babyhood.

Ingredients: WATER, CARROTS, GROUND CHICKEN, RICE FLOUR, ENRICHED EGG NOODLES (DURUM WHEAT SEMOLINA, EGG YOLK SOLIDS, NIACIN, FERROUS SULFATE, THIAMIN MONONITRATE, RIBOFLAVIN, FOLIC ACID), CHICKEN FAT, PEAR JUICE CONCENTRATE, ONION POWDER, BALSAMIC VINEGAR, DRIED PARSLEY.

Nutrition Facts
  Serv. Size 1 jar
  Servings Per Container: 1
  Amount Per Serving
  Calories 120
  Total Fat: 3 g
  Trans Fat: 0 g
  Sodium: 45 mg
  Potassium: 200 mg
  Total Carbohydrates: 18 g
  Fiber: 2 g
  Sugars: 4 g
  Protein: 4 g
  % Daily Value

| | |
|---|---|
| Protein: 21% | Vitamin A: 290% |
| Vitamin C: 0% | Calcium: 4% |
| Iron: 4% | Zinc: 15% |

Example 2

This example investigates the effect of feeding diets supplemented or not with ARA to newborn guinea pig pups on the development of total fat mass of the pups in the post-weaning period. The infant guinea pig is considered to be a good animal model to study the development fat mass in human infants: Indeed, like newborn human infants, guinea pig pups are born with an appreciable amount of body fat whilst newborn rat and mice pups are very lean.

Study Design:

Newborn male guinea pigs were divided into two groups with 20 animals per group. Each group was fed a suckling/weaning diet in which 44% of the energy was supplied by fat for 21 days. The different diets were isocaloric and differed only in their ARA contents. The ARA diet contained 1.5% ARA based on total fatty acids and the control diet contained no ARA. The group receiving ARA diet is coded "ARA diet" or "+AA" in the below and in the figures. The group receiving no ARA is coded "control diet" or "−AA" in the below and in the figures. The levels of linoleic acid and α-linolenic acid were kept relatively constant between the diets such that the ratio of linoleic acid to α-linolenic acid was about 35. Further details of the fatty acid composition of the two diets are given in Table 1.

TABLE 1

Fatty acid composition of the suckling/weaning diets:

| % of total fatty acids | Control Diet | ARA Diet |
|---|---|---|
| C12:0 | 7.9 | 6.6 |
| C14:0 | 3.7 | 3.3 |
| C16:0 | 21.8 | 22.2 |
| C16:1 | 0.1 | 0.1 |
| C18:0 | 3.0 | 3.4 |
| C18:1 | 33.3 | 33.5 |
| C18:2n-6 (LA) | 28.5 | 27.9 |
| C18:3n-3 (ALA) | 0.8 | 0.8 |
| C20:0 | 0.0 | 0.0 |
| C20:1 | 0.0 | 0.0 |
| C20:4n-6 (ARA) | 0.0 | 1.5 |

TABLE 1-continued

Fatty acid composition of the suckling/weaning diets:

| % of total fatty acids | Control Diet | ARA Diet |
|---|---|---|
| C20:5n-3 | 0.0 | 0.0 |
| C22:0 | 0.0 | 0.0 |
| C22:5n-3 | 0.0 | 0.0 |
| C22:6n-3 (DHA) | 0.0 | 0.0 |

At the end of the suckling/weaning period (day 21), both groups were fed a diet with a moderately high fat content (35% of energy from fat) containing no ARA until day 136. Body weight and fat mass were recorded at days 21, 51, 79, 107, 128 and 136 and plasma fatty acid composition, and plasma insulin concentrations were recorded at day 21 and day 136.

Results:

As expected, the group supplemented with ARA showed higher incorporation of ARA in plasma phospholipids (Table 2) and triglycerides (Table 3) than the control group.

TABLE 2

Fatty acid (µg/ml) composition in plasma phospholipids at d21. Mean ± SEM

| | Control Diet | ARA Diet |
|---|---|---|
| C10:0 | 0.1 ± 0.07 | 0.1 ± 0.01 |
| C12:0 | 0.3 ± 0.13 | 0.2 ± 0.01 |
| C14:0 | 1.1 ± 0.17 | 0.8 ± 0.13 |
| C16:0 | 40.2 ± 3.6 | 37.8 ± 3.4 |
| C17:0 | 1.2 ± 0.10 | 1.1 ± 0.29 |
| C18:0 | 68.6 ± 4.2 | 83.6 ± 4.6 |
| C18:1 n-9 cis + trans | 23.2 ± 1.9 | 24.9 ± 1.8 |
| C18:1 n-7 cis + trans | 5.2 ± 0.9 | 4.3 ± 0.3 |
| C18:2 n-6 (LA) | 77.0 ± 7.5 | 61.5 ± 4.3 |
| C18:3n-6 (GLA) | 0.2 ± 0.13 | 0.1 ± 0.04 |
| C18:3n-3 (ALA) | 0.6 ± 0.2 | 0.4 ± 0.14 |
| C20:0 | 0.9 ± 0.03 | 1.0 ± 0.05 |
| C20:1n-9 | 0.6 ± 0.1 | 0.5 ± 0.03 |
| C20:2n-6 | 1.3 ± 0.2 | 1.0 ± 0.05 |
| C20:3n-6 | 1.0 ± 0.07 | 1.1 ± 0.06 |
| C20:4n-6 (ARA) | 11.7 ± 1.1$^a$ | 40.7 ± 3.2$^b$ |
| C20:3n-3 | 0.1 ± 0.03 | 0.4 ± 0.02 |
| C22:0 | 1.1 ± 0.2 | 1.2 ± 0.08 |
| C22:1n-9 | 1.5 ± 1.0 | 0.3 ± 0.02 |
| C20:5n-3 (EPA) | 0.1 ± 0.03 | ND |
| C22:2n-6 | 0.8 ± 0.1 | 0.8 ± 0.06 |
| C22:4n-6 | 1.2 ± 0.2$^a$ | 2.8 ± 0.1$^b$ |
| C24:0 | 1.9 ± 0.4 | 2.3 ± 0.1 |
| C24:1n-9 | 2.0 ± 0.5 | 1.8 ± 0.1 |
| C22:5n-3 (DPA) | 0.9 ± 0.1 | 0.7 ± 0.09 |
| C22:6n-3 (DHA) | 0.7 ± 0.1 | 0.6 ± 0.06 |

Different letters indicate statistical significance at $P < 0.05$,
ND; not detectable

TABLE 3

Fatty acid (µg/ml) composition in plasma triglycerides at d21. Mean = SEM

| | Control Diet | ARA Diet |
|---|---|---|
| C10:0 | 0.2 ± 0.01 | 0.2 ± 0.09 |
| C12:0 | 0.8 ± 0.3 | 0.8 ± 0.1 |
| C14:0 | 4.0 ± 2.4 | 4.1 ± 0.7 |
| C16:0 | 42.2 ± 18 | 57.5 ± 3.2 |
| C17:0 | 0.7 ± 0.09 | 1.0 ± 0.1 |
| C18:0 | 10.5 ± 3.5 | 16.7 ± 4.6 |
| C18:1 n-9 cis | 63.2 ± 18 | 88.7 ± 16.1 |
| C18:1 n-7 cis | 2.0 ± 0.6 | 2.7 ± 0.5 |
| C18:2 n-6 (LA) | 71.1 ± 27.9 | 87.0 ± 14.5 |
| C18:3n-6 (GLA) | 0.5 ± 0.1 | 0.9 ± 0.1 |

TABLE 3-continued

Fatty acid (µg/ml) composition in plasma
triglycerides at d21. Mean = SEM

| | Control Diet | ARA Diet |
|---|---|---|
| C18:3n-3 (ALA) | 2.7 ± 0.2 | 3.9 ± 0.6 |
| C20:0 | 0.2 ± 0.1 | 0.7 ± 0.1 |
| C20:1n-9 | 1.1 ± 0.5 | 1.1 ± 0.1 |
| C20:2n-6 | 1.6 ± 0.8 | 1.4 ± 0.2 |
| C20:3n-6 | 0.6 ± 0.09 | 1.1 ± 0.1 |
| C20:4n-6 (ARA) | 3.7 ± 0.3$^a$ | 13.3 ± 1.2$^b$ |
| C20:3n-3 | 0.1 ± 0.09 | 0.2 ± 0.07 |
| C22:0 | 0.3 ± 0.02 | 0.4 ± 0.04 |
| C22:1n-9 | 0.2 ± 0.03 | 0.2 ± 0.04 |
| C20:5n-3 (EPA) | 0.1 ± 0.08 | 0.1 ± 0.04 |
| C22:2n-6 | 0.2 ± 0.08 | 0.2 ± 0.02 |
| C22:4n-6 | 0.9 ± 0.2 | 1.8 ± 0.26 |
| C24:0 | 0.6 ± 0.1 | 0.8 ± 0.1 |
| C22:5n-3 (DPA) | 0.4 ± 0.01 | 0.4 ± 0.07 |
| C22:6n-3 (DHA) | 0.2 ± 0.05 | 0.2 ± 0.1 |

Different letters indicate statistical significance at $P < 0.05$,
ND; not detectable As may be seen from FIG. 1, mean body weight did not differ significantly between the groups during the course of the experiment.

At the end of the suckling/weaning period (day 21), total fat mass measured by NMR did not differ between the groups.

Surprisingly, after the end of the suckling/weaning period and as may be seen from FIGS. 2 and 3, the ARA group (coded "+AA") had lower fat mass in both gram and percentage terms than the control group (coded "−AA).

Plasma insulin levels were not different between groups at day 21. However, as shown in FIG. 4, at the end of the experiment, the ARA group showed about a 1.6-fold lower concentration of plasma insulin compared to the control group. FIG. 5 shows that similar results were observed regarding the pancreatic insulin content. The ARA group showed about a 1.6-fold decrease in the pancreatic insulin content when compared to the control group. Plasma glucose levels were not different between groups at either d21 or d136 (data not shown).

Without being bound by the theory, this example clearly demonstrates that feeding a diet enriched in ARA during infancy plays an important role in programming or imprinting the adipose tissue in such a way as to reduce its susceptibility to excessive development later in life. Specifically, the results indicate that a moderate ARA intake during the suckling/weaning period decreased adiposity and insulin resistance, later in life.

The invention claimed is:

1. A nutritional composition for a mammal, the nutritional composition comprising:
    a protein source that is less than 1.85 g/100 kcal of the nutritional composition;
    a lipid source in an amount of 4.4 to 6 g/100 kcal of the nutritional composition, the lipid source comprising linoleic acid (LA) and α-linolenic acid (ALA) in a ratio of LA:ALA less than 7:1;
    a carbohydrate source; and
    arachidonic acid (ARA) in an amount from 1.5% to 2% of total fatty acid content of the nutritional composition, and the nutritional composition not containing docosahexaenoic acid.

2. The nutritional composition of claim 1, wherein the composition comprises between 0.3 mg and 0.7 mg of arachidonic acid per kcal of the nutritional composition.

3. The nutritional composition of claim 1 wherein the composition is in a form selected from the group consisting of an infant formula, a follow-on formula, and a growing-up milk.

* * * * *